(12) United States Patent
San et al.

(10) Patent No.: US 7,326,557 B2
(45) Date of Patent: Feb. 5, 2008

(54) INCREASING INTRACELLULAR NADPH AVAILABILITY IN E. COLI

(75) Inventors: Ka-Yiu San, Houston, TX (US); George N. Bennett, Houston, TX (US); Ailen Sanchez, Houston, TX (US)

(73) Assignee: Rice University, Houston, TX (US)

(*) Notice: Subject to any disclaimer, the term of this patent is extended or adjusted under 35 U.S.C. 154(b) by 208 days.

(21) Appl. No.: 10/987,265

(22) Filed: Nov. 12, 2004

(65) Prior Publication Data
US 2005/0196866 A1    Sep. 8, 2005

Related U.S. Application Data

(60) Provisional application No. 60/520,540, filed on Nov. 14, 2003.

(51) Int. Cl.
| | |
|---|---|
| C12N 1/12 | (2006.01) |
| C12N 15/63 | (2006.01) |
| C12Q 1/68 | (2006.01) |
| G01N 33/554 | (2006.01) |
| C07H 21/02 | (2006.01) |

(52) U.S. Cl. ............... 435/252.3; 435/6; 435/7.32; 435/320.1

(58) Field of Classification Search ............ None
See application file for complete search history.

(56) References Cited

U.S. PATENT DOCUMENTS 6,455,284 B1    9/2002    Gokarn et al.

OTHER PUBLICATIONS

Lim et al. Amplification of the NADPH-Related Genes zwf and gnd for th Oddball Biosynthesis of PHB in an *E. coli* Tranformant Harboring a Cloned phbCAB Operon. J. Bioscience and Bioengineering. 93(6): 543-549. 2002.*

Canonaco et al. Metabolic flux response to phosphoglucose isomerase knock-out in *Escherichia coli* and impact of overexpression of the soluble transhydrogenase UdhA. FEMS Micro. Letters. 204: 247-252. 2001.*

Maicas, S et al., NAD(P)H regeneration is the key for heterolactic fermentation of hexoses in *Oenococcus oeni*, Microbiology, Jan. 2002;148(Pt 1):325-32.

Verho, R. et al., Engineering redox cofactor regeneration for improved pentose fermentation in *Saccharomyces cerevisiae*, Appl, Environ Microbiol. Oct. 2003;69(10):5892-7.

* cited by examiner

*Primary Examiner*—David Guzo
*Assistant Examiner*—Michele K. Joike
(74) *Attorney, Agent, or Firm*—Baker & McKenzie LLP

(57) ABSTRACT

A method of increasing cellular NADPH levels by expressing one or more genes that encode a enzyme that causes the production of NADPH. The system can be combined with other enzymes that require NADPH, thus improving the overall production of the desired protein.

12 Claims, 1 Drawing Sheet

INCREASING INTRACELLULAR NADPH AVAILABILITY IN E. COLI

PRIOR RELATED APPLICATIONS

This application claims the benefit of U.S. Provisional Application No. 60/520,540 filed Nov. 14, 2003.

REFERENCE TO MICROFICHE APPENDIX

Not applicable.

FEDERALLY SPONSORED RESEARCH STATEMENT

The present invention was developed with funds from the National Science Foundation. Therefore, the United States Government may have certain rights in the invention.

FIELD OF THE INVENTION

The invention relates to a technique for metabolically engineering *Escherichia coli* (*E. coli*) strains to provide increased intracellular NADPH availability by means of channeling increased NADH levels to NADPH for the purpose of increasing the yield and productivity of NADPH-dependent compounds.

BACKGROUND OF THE INVENTION

Numerous bioproducts including primary and secondary metabolites, recombinant proteins, and other biopolymers are produced by microbial fermentation. However, natural organisms are not optimized for this task, and therefore microorganisms are often engineered to enhance their metabolic capacities.

The cofactor pair NADPH/NADP+ is essential for all living organisms. Their importance centers mainly on their use as donors and/or acceptors of reducing equivalents in many oxidation-reduction reactions in living cells. The NADH/NAD+ pair is used for catabolic activities of the cell, whereas anabolic metabolism specifically requires NADPH/NADP+. Together, these nucleotides have a direct impact on virtually every oxidation-reduction metabolic pathway in the cell.

Many industrially useful compounds require NADPH for their synthesis. Due to the high cost and regeneration difficulty of these coenzymes, the enzymatic production of cofactor-dependent compounds has proved to be challenging.

Polyhydroxyalkanoates (PHAs) are a family of biodegradable polyesters synthesized by numerous microorganisms and function as an intracellular carbon and energy storage material. The best characterized member of PHA is poly(3-hydroxybutyric acid), PHB. PHB is synthesized from acetyl-CoA in three sequential reaction steps catalyzed by the enzymes of the phb operon, β-ketothiolase, acetoacetyl-CoA reductase and PHB synthase. The second reaction catalyzed by the reductase requires NADPH as a cofactor. In other words, the requirement for NADPH plays a key role in the biosynthesis of important metabolites such as PHB.

NADH/NADP+ transhydrogenase, the enzyme responsible for the conversion of NADH to NADPH, can be induced in *E. coli* strains following exposure to agents, such as $H_2O_2$. This represents one method of increasing the intracellular levels of NADPH. However, such methods are not useful due to the deleterious effects of the agents. Therefore, methods of increasing the intracellular levels of the cofactor NADPH is required that do not otherwise damage the cell or detract from its ability to produce large amounts of desirable protein.

SUMMARY OF THE INVENTION

The invention generally relates to a method of increasing the NADPH levels in a bacterial cell, comprising providing a bacterial host cell, transforming the host cell with an expression vector encoding an enzyme that catalyzes the following reaction:

$$NADH + NADP^+ \longleftrightarrow NAD^+ + NADPH$$

such that the bacterial host cell produces more NADPH after transformation than it did prior to transformation. The cell will produce at least 50% more NADPH after engineering than it did before engineering. In preferred embodiments, it will produce at least 75% more, 100% more, or 150% more NADPH.

In certain embodiments of the invention, the enzyme catalyzing the above conversion is overexpressed.

In certain embodiments of the invention the gene encoding pyridine nucleotide transhydrogenase (udhA) is transformed into a test *E. coli* strain. In other embodiments of the invention, the gene encoding formate dehydrogenase is introduced into an *E. coli* strain.

DESCRIPTION OF EMBODIMENTS OF THE INVENTION

Figure 1:
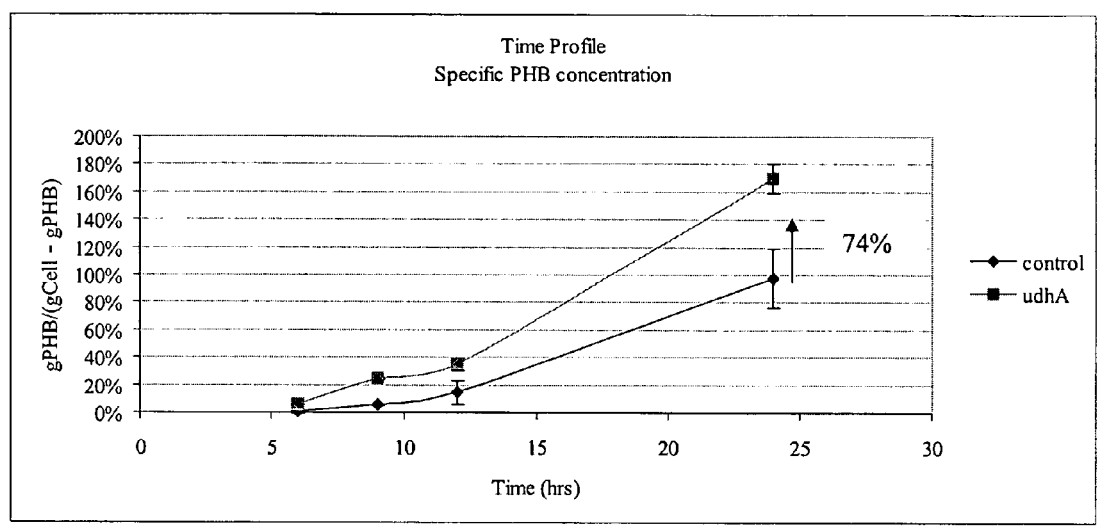
FIG. 1. illustrates the amount of PHB produced over time in a control host cell and a host cell transformed with udhA.

By "overexpresses" what is meant herein is either that there is more protein or more protein activity.

The invention generally relates to the construction of genetically engineered strains capable of increasing intracellular NADPH availability by channeling the reducing equivalents from NADH. Increased NADPH availability can be further utilized to improve the productivity and yield of products requiring this cofactor.

An embodiment of the invention is designed to increase the intracellular availability of NADPH. An increase in the intracellular availability of NADPH allows the increase of products that require this cofactor in their biosynthesis pathways. An example of such a product is poly(3-hydroxybutyrate) or PHB. Other applications include the production of amino acids and other biosynthetic products, biodegradation of toxic chemicals and others.

The novelty of the present system is that a new approach to increase the availability of NADPH has been achieved by genetic engineering means. The levels may be manipulated by changing the expression levels of selected enzymes or the quantity of supplied substrate.

To achieve these goals, bacterial cells are transformed with a plasmid carrying the gene encoding soluble pyridine nucleotide transhydrogenase, udhA. Pyridine nucleotide transhydrogenase catalyzes the reversible transfer of a hydride ion equivalent between NAD and NADP. The enzyme functions as a proton pump, translocating protons from the cytosolic side of the membrane to the outside.

In certain embodiments of the invention, a source of NADH is additionally provided to a bacterial cell transformed with udhA.

NADPH is normally generated through the oxidative part of the pentose phosphate pathway by the action of glucose-6-phosphate dehydrogenase (GDH):

Glucose+NADP+→gluconolactone-6-P+NADPH+H+

However, there are many other ways of generating NADPH. For example, GDH could be activated or overexpressed to increase NADPH production according to the following reaction:

Glucose+NADP+→d-glucolactone+NADPH

Other enzymes that may be used to increase NADPH production include, but are not limited to, formate dehydrogenase, glucose-6-phosphate dehydrogenase, mannitol dehydrogenase, erythritol-4-phosphate dehydrogenase, and pyridine nucleotide transhydrogenase. Also included are NADPH forming GAPDH enzymes, such as glyceraldehyde phosphate dehydrogenase that act on NADPH to replace or add to the NADH forming activity of NADH dependent GAPDH enzymes.

In certain embodiments of the invention, proteins from other species may also be used. For example, the soluble pyridine nucleotide transhydrogenase of *Pseudomonas fluorescens* can been used in a cell-free system for the regeneration of the nicotinamide cofactors NAD and NADP in the biological production of the important semisynthetic opiate drug hydromorphone.

EXAMPLE 1

A novel approach to increase the NADPH in vivo through metabolic and genetic engineering. In this approach a soluble pyridine nucleotide transhydrogenase is overexpressed. This soluble enzyme catalyzes the reversible transfer of reducing equivalents between NAD and NADP according to the following equation:

$$NADH + NADP^+ \leftrightarrow NAD^+ + NADPH$$

In addition, NADPH availability can be further increased by the following scheme using a NADH regeneration system:

The functionality of this NADPH enhancement system was tested using the production of PHB as a model system since one of the PHB biosynthesis steps involves the use of NADPH. An *E. coli* strain harboring a two plasmid system was constructed, one encoding the udhA gene and the second encoding the phb operon.

As shown in FIG. 1, the functionality of the two plasmid particular system was successfully demonstrated in these PHB production experiments. The results showed that both productivity and yield were increased significantly. The PHB productivity of the strain carrying both the udhA gene and the phb operon increased by 74% when compared to that of the control strain carrying only the phb operon.

Further improvement of increasing NADPH availability, which subsequently leads to higher productivities of the desired product, can be achieved by supplying a source of NADH to the system. For example, as shown above, NADH can be regenerated from formate by overexpressing the NAD+-dependent formate dehydrogenase (FDH). Addition of NADH to NADP+ in the presence of pyridine nucleotide transhydrogenase results in the production of NADPH. It is predicted that yield can be improved 100% or more with additional optimization.

The invention claimed is:

1. A method of increasing the NADPH levels in a bacterial cell, comprising
    a) providing a bacterial host cell,
    b) transforming the host cell with an expression vector encoding a pyridine nucleotide transhydrogenase that catalyzes the following reaction:

$$NADH + NADP^+ \leftrightarrow NAD^+ + NADPH$$

and,
    c) transforming the host cell with one or more genes that encode at least one enzyme that uses NADPH as a cofactor,
wherein the bacterial host cell produces at least 50% more NADPH after transformation than it did prior to transformation.

2. The method of claim 1, wherein at least one enzyme is overexpressed.

3. The method of claim 2, wherein at least one enzyme is selected from the group consisting of formate dehydrogenase, glucose-6 phosphate dehydrogenase, mannitol dehydrogenase, erythritol-4-phosphate dehydrogenase, glucose dehydrogenase (GDH) and NADPH forming glyceraldehyde phosphate dehydrogenase.

4. The method of claim 3, wherein the host cell is *E. coli*.

5. The method of claim 1, wherein the genes are the PHB operon.

6. A genetically engineered cell that produces more NADPH than the same cell prior to genetic engineering, wherein said cell comprises one or two expression vectors encoding:
    a) a pyridine nucleotide transhydrogenase; and
    b) phb operon including β-ketothiolase, acetoacetyl-CoA reductase and PHB synthase, wherein said cell increases NADPH production as measured by increased PHB synthesis.

7. The genetically engineered cell of claim 6, that produces at least 50% more NADPH than the same cell prior to genetic engineering.

8. The genetically engineered cell of claim 6, that produces at least 75% more NADPH than the same cell prior to genetic engineering.

9. The genetically engineered cell of claim 8, that is a bacterial cell.

10. The genetically engineered cell of claim 9, additionally comprising an enzyme selected from the group consisting of formate dehydrogenase, glucose-6-phosphate dehydrogenase, mannitol dehydrogenase, erythritol-4-phosphate dehydrogenase, and glucose dehydrogenase, wherein the enzyme is overexpressed.

11. The genetically engineered cell of claim 6, comprising an *E. coli* cell that overexpresses pyridine nucleotide transhydrogenase.

12. A genetically engineered bacterial cell, comprising overexpression of pyridine nucleotide transhydrogenase so that at least 50% more NADPH is expressed in said cell as compared with the same cell prior to genetic engineering; and overexpression of one or more genes that encode at least one enzyme that uses NADPH as a cofactor.

* * * * *

UNITED STATES PATENT AND TRADEMARK OFFICE
CERTIFICATE OF CORRECTION

| | | |
|---|---|---|
| PATENT NO. | : 7,326,557 B2 | Page 1 of 1 |
| APPLICATION NO. | : 10/987265 | |
| DATED | : February 5, 2008 | |
| INVENTOR(S) | : Ka-Yiu San et al. | |

It is certified that error appears in the above-identified patent and that said Letters Patent is hereby corrected as shown below:

Col. 1 line 19 please insert the following paragraph prior to the heading FIELD OF THE INVENTION:

--FEDERALLY SPONSORED RESEARCH STATEMENT
This invention was made with government support under Grant No.: BES-0000303 awarded by National Science Foundation. The government has certain rights in the invention.--

Signed and Sealed this

Thirty-first Day of January, 2012

David J. Kappos
*Director of the United States Patent and Trademark Office*